(12) United States Patent
Chen et al.

(10) Patent No.: US 10,377,986 B2
(45) Date of Patent: Aug. 13, 2019

(54) THREE-DIMENSIONAL SILK FIBROIN SCAFFOLD CULTURE RETAINING FUNCTIONAL SALIVARY CELLS AND PROMOTING SALIVARY TISSUE-SPECIFIC ECM SYNTHESIS

(71) Applicant: THE BOARD OF REGENTS OF THE UNIVERSITY OF TEXAS SYSTEM, Austin, TX (US)

(72) Inventors: Xiao-Dong Chen, San Antonio, TX (US); Chih-ko Yeh, San Antonio, TX (US); Joo L. Ong, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 77 days.

(21) Appl. No.: 15/118,539

(22) PCT Filed: Feb. 9, 2015

(86) PCT No.: PCT/US2015/014994
§ 371 (c)(1),
(2) Date: Aug. 12, 2016

(87) PCT Pub. No.: WO2015/123132
PCT Pub. Date: Aug. 20, 2015

(65) Prior Publication Data
US 2017/0056557 A1    Mar. 2, 2017

Related U.S. Application Data

(60) Provisional application No. 61/938,889, filed on Feb. 12, 2014.

(51) Int. Cl.
*C12N 5/071* (2010.01)
*A61L 27/38* (2006.01)
*A61L 27/22* (2006.01)

(52) U.S. Cl.
CPC ........ *C12N 5/0633* (2013.01); *A61L 27/3813* (2013.01); *A61L 27/227* (2013.01); *C12N 2501/999* (2013.01); *C12N 2533/50* (2013.01); *C12N 2533/52* (2013.01); *C12N 2533/56* (2013.01)

(58) Field of Classification Search
CPC ............. A61L 27/3604; A61L 27/3813; A61L 27/3689; C12N 5/0633
See application file for complete search history.

(56) References Cited

U.S. PATENT DOCUMENTS

| | | | | |
|---|---|---|---|---|
| 4,829,000 A * | 5/1989 | Kleinman | ............... | A61K 35/50 435/267 |
| 2006/0273279 A1 | 12/2006 | Kaplan et al. | ..................... | 252/1 |
| 2011/0008892 A1 * | 1/2011 | Nigam | .................. | C12N 5/0686 435/377 |
| 2011/0293666 A1 | 12/2011 | Wang et al. | .................... | 424/400 |
| 2012/0183987 A1 | 7/2012 | Gevaert et al. | .................. | 435/29 |
| 2013/0210049 A1 * | 8/2013 | Larsen | ................. | C12N 5/0068 435/22 |

FOREIGN PATENT DOCUMENTS

WO    WO 2013/071123    *    5/2013    ............. A61L 27/22

OTHER PUBLICATIONS

"fibroid". Dictionary.com Unabridged. Random House, Inc. Apr. 12, 2018. <Dictionary.com http://www.dictionary.com/browse/fibroid>. (Year: 2018).*
Laoide et al, "Immortalised mouse submandibular epithelial cell lines retain polarised structural and functional properties" J Cell Sci, 1996, vol. 109, pp. 2789-2800. (Year: 1996).*
Zhu et al, "The Preparation of Silk Fibroin Modified PBT-co-PBS/PEG Composite Films and their Effects on Clinical Human Salivary Epithelial Cells Transplantation." J Biomim Biomater Tissue Eng Jul. 2013, vol. 18, p. 1-7. (Year: 2013).*
Szlavik et al "Matrigel-Induced Acinar Differentiation is Followed by Apoptosis in HSG Cells" Journal of Cellular Biochemistry, 2008, vol. 103, pp. 284-295. (Year: 2008).*
Aframian et al., "Current status of the development of an artificial salivary gland." Tissue Eng Part B Rev. vol. 14, No. 2, 2008, pp. 187-198.
Athanasiou et al., "Sterilization, toxicity, biocompatibility and clinical applications of polylactic acid/polyglycolic acid copolymers." Biomaterials. vol. 17, No. 2, 1996, pp. 93-102.
Busch et al., "Differences in the regulatory mechanism of amylase release by rat parotid and submandibular glands." Arch Oral Biol. vol. 47, No. 10, 2002, pp. 717-722.
Cancedda et al., "Tissue engineering and cell therapy of cartilage and bone." Matrix Biol. vol. 22, No. 1, 2003, pp. 81-91.
Chan et al., "Formation of post-confluence structure in human parotid gland acinar cells on PLGA through regulation of E-cadherin." Biomaterials. vol. 33, No. 2, 2012, pp. 464-472.
Chen, "Extracellular matrix provides an optimal niche for the maintenance and propagation of mesenchymal stem cells." Birth Defects Res C Embryo Today. vol. 90, No. 1, 2010, pp. 45-54.
Chen et al., J Bone Miner Res. 22(12):1943-56, 2007.
Chen et al., "Proliferation and phenotypic preservation of rat parotid acinar cells." Tissue Eng. vol. 11, Nos. 3-4, 2005, pp. 526-534.
Coppes et al., "Stem cells and the repair of radiation-induced salivary gland damage." Oral Dis. vol. 17, No. 2, 2011, pp. 143-153.
Costa et al., "Biophysical signals controlling cell fate decisions: how do stem cells really feel?" Int J Biochem Cell Biol. vol. 44, No. 12, 2012, pp. 2233-2237.

(Continued)

*Primary Examiner* — Allison M Fox
(74) *Attorney, Agent, or Firm* — Norton Rose Fulbright US LLP

(57) ABSTRACT

A cell culture system including a silk fibroid scaffold, culture media, and salivary gland cells. The salivary gland cells grown in the tissue culture system have physiological and morphological features like those of in vivo salivary gland cells. The cell culture system can be used to produce a salivary tissue-specific extracellular matrix capable of inducing differentiation of salivary gland cell precursors into salivary gland cells.

11 Claims, 9 Drawing Sheets

(56) References Cited

OTHER PUBLICATIONS

Crapo et al., Biomaterials. 32(12):3233-43, 2011.
D'Avola et al., "Three-dimensional characteristics of submandibular salivary gland of ageing rats: an HRSEM study." Ann Anat. vol. 188, No. 5, 2006, pp. 431-438.
De Moraes et al., "Effects of sterilization methods on the physical, chemical, and biological properties of silk fibroin membranes." J Biomed Mater Res B Appl Biomater. vol. 102, No. 4, 2014, pp. 869-876.
Fujita-Yoshigaki et al., "A primary culture of parotid acinar cells retaining capacity for agonists-induced amylase secretion and generation of new secretory granules." Cell Tissue Res. vol. 320, No. 3, 2005, pp. 455-464.
Ghorbanianet et al., "Fabrication and characterization of novel diopside/silk fibroin nanocomposite scaffolds for potential application in maxillofacial bone regeneration" Int J Biol Macromol. 58:275-80, 2013.
Harunaga et al., J Dent Res. 90(9):1070-7, 2011.
International Preliminary Report on Patentability in International Application No. PCT/US2015/014994 dated Aug. 25, 2016.
International Search Report and Written Opinion in International Application No. PCT/US2015/014994 dated Apr. 28, 2015.
Kadoya et al., "Salivary gland morphogenesis and basement membranes." Anat Sci Int. vol. 80, No. 2, 2005, pp. 71-79.
Kagami et al., "Restoring the function of salivary glands." Oral Dis. vol. 14, No. 1, 2008, pp. 15-24.
Kundu et al., "Silk proteins for biomedical applications: Bioengineering perspectives," Progress in Polymer Science. vol. 39, No. 2, 2014, pp. 251-267.
Lai et al., Stem Cells Dev. 19(7):1095-107, 2010.
Leal-Egana et al., "Silk-based materials for biomedical applications." Biotechnol Appl Biochem. vol. 55, No. 3, 2010, pp. 155-167.
Lombaert et al., Oral Dis. 17(5):445-9, 2011.
Maria et al., "Matrigel improves functional properties of primary human salivary gland cells." Tissue Eng Part A. vol. 17, Nos. 9-10, 2011, pp. 1229-1238.
Marmary et al., "Fluid secretion rates from mouse and rat parotid glands are markedly different following pilocarpine stimulation." Comp Biochem Physiol A Comp Physiol. vol. 88, No. 2, 1987, pp. 307-310.
Mauney et al., Biomaterials. 28: 5280, 2007.
Nagaoka et al., "Application of recombinant fusion proteins for tissue engineering." Ann Biomed Eng. vol. 38, No. 3, 2010, pp. 683-693.
Napenas et al., "Diagnosis and treatment of xerostomia (dry mouth)." Odontology. vol. 97, No. 2, 2009, pp. 76-83.
Siritientong et al., AAPS PharmSciTech. 12: 771, 2011.
Sofia et al., "Functionalized silk-based biomaterials for bone formation." J Biomed Mater Res. vol. 54, No. 1, 2001, pp. 139-148.
Widhe et al., "Recombinant spider silk as matrices for cell culture." Biomaterials. vol. 31, No. 36, 2010, pp. 9575-9585.
Yeh et al., "Cellular characteristics of long-term cultured rat parotid acinar cells." In Vitro Cell Dev Biol. vol. 27A, No. 9, 1991, pp. 707-712.
Zhang et al., J Biol Chem. 283(12):7580-9, 2008.

\* cited by examiner

THREE-DIMENSIONAL SILK FIBROIN SCAFFOLD CULTURE RETAINING FUNCTIONAL SALIVARY CELLS AND PROMOTING SALIVARY TISSUE-SPECIFIC ECM SYNTHESIS

This application is a national phase application under 35 U.S.C. § 371 of International Application No. PCT/US2015/014994, filed Feb. 9, 2015 which claims priority to U.S. Provisional Patent Application Ser. No. 61/938,889, filed Feb. 12, 2014. Both applications are hereby incorporated in their entirety.

BACKGROUND OF THE INVENTION

1. Field of the Invention

The present invention relates generally to the field of cell biology. More particularly, it concerns cell culture systems for salivary gland cells and production and use of salivary tissue-specific extracellular matrices for growth and differentiation of cells.

2. Description of Related Art

Salivary gland hypofunction is usually associated with xerostomic medications, radiotherapy to head and neck regions, autoimmune diseases (e.g., Sjögren's syndrome), aging, and systemic diseases such as diabetes, mellitus and renal diseases (Napenas, et al., 2009), which usually leads to rampant and severe oral diseases with compromised quality of life. Unfortunately, adult salivary glands are highly differentiated and show little regenerative capacity in response to physical (e.g. radiation) and pathological (e.g. Sjögren's syndrome) assaults. Therefore, development of strategies to preserve or regain secretory components in the salivary gland is essential for the management of patients with salivary diseases. Development of these treatment strategies requires the establishment of a system capable of replicating the salivary gland cell "niche" to support the proliferation and differentiation of salivary gland progenitor cells. The potential approaches for restoring the function of salivary glands include 1) inserting genes into residual salivary acinar or ductal cells, 2) replacing the salivary gland with functional artificial tissue, and 3) regrowing the salivary gland tissue in situ (Baum, 2000). The former can be achieved by gene transfer, but the latter 2 approaches will require extensive knowledge of stem cells and tissue engineering technologies. Reconstruction of salivary glands is a complex process that involves cell-cell communication, cell-matrix interaction and cell signal transduction in a 3-dimensional (3D) structure. To achieve these complex biological processes, several parallel lines of regeneration research have focused on identifying and/or isolating salivary stem/progenitor cells (Lombaert, et al., 2011; Kagami, et al., 2008), elucidating pathways and factors associated with salivary gland development (Harunaga, et al., 2011), and developing appropriate biomaterial scaffolds that support the proliferation and differentiation of salivary gland progenitors (Aframian & Palmon, 2008; Chan, et al., 2012).

Extracellular matrix (ECM) is an important component of the cellular niche in tissues, supplying critical biochemical and physical signals to initiate or sustain cellular functions (Chen, et al., 2008; Lai, et al., 2010). With advances in tissue engineering, the various scaffold biomaterials have been developed to mimic ECMs for tissue regeneration or repair (Nagaoka, et al., 2010). Among them, the materials that have been use to support the proliferation and differentiation of salivary gland progenitors include chitosan, polyglycolic acid (PGA), poly-(1)-lactic acid (PLLA), poly (lactic-co-glycolic acid) (PLAG), poly(ethylene glycol)-terephthalate (PEFT/poly (butylene terephthalate (PBT) (Kagami, et al., 2008; Chan, et al., 2012; Chen, et al., 2005). However, these polymeric scaffolds can induce inflammation resulting from the acidity of their degradation products (Athanasiou, et al., 1996; Cancedda, et al., 2003). Another potential scaffold material, Matrigel, which contains basement membrane proteins secreted by EHS mouse sarcoma cells, has been used to grow primary salivary gland epithelial cells in culture (Maria, et al., 2011). Although varying levels of success have been achieved with this product, it is not consistent with the long term goal to reconstitute the salivary gland niche (tissue-specific ECM) on a scaffold for controlling stem cell fate. Natural scaffold materials, especially silk, are desirable due to their wide ranges of elasticity (allowing tissue-specific scaffold formation), pore sizes (allowing tissue specific nutrition and oxygen access), low bacterial adherence, biodegradable, and low toxicity and immunogenicity (Leal-Egana & Scheibel, 2010).

Adult salivary glands are known to contain progenitor and stem cells that can be directed to salivary tissue differentiation or other tissue types depending on the tissue-specific microenvironment or niche that is mainly made up of ECM proteins associated with growth factors (Coppes & Stokman, 2011). Currently, the 3-D matrixes used for in vitro salivary cell growth and differentiation systems are either unpractical for clinical use, e.g., as tumor cell produced Matrigel, or only have one or two basement membrane components (Maria, et al., 2011). Basement membrane is critical for epithelial cell polarization and differentiation and has been demonstrated to play a key role during salivary gland development (Kadova & Yamashina, 2005). A tissue-specific ECM microenvironment is essential to provide chemical and physical cues to direct/govern multipotent stem cells in vivo and in vitro for tissue regeneration and repair (Chen, 2010; Costa, et al., 2012).

There remains a need for a tissue culture system to allow growth of salivary gland cells in such a way that they retain physiologically relevant features of salivary gland cell function. Also desirable are salivary gland tissue-specific three-dimensional (3D) scaffolds for salivary gland tissue engineering. Salivary gland-specific extracellular matrices can be used to differentiate salivary gland cell progenitors, including pluripotent stem cells, into salivary gland cells and to grow salivary gland tissue that can be used in a variety of therapies.

SUMMARY OF THE INVENTION

Disclosed herein is a cell culture system comprising a silk fibroin scaffold, culture media, and salivary gland cells. In some embodiments, the silk fibroin scaffold is coated with fibronectin. The silk fibroin scaffold may also be depleted of any allergens or other substances harmful to mammals, including sericins, before being used in the cell culture systems or in the creation of the extracellular matrices of the present invention. A variety of different salivary gland cell types may be used in the cell culture system. For example, in some embodiments the salivary gland cells comprise parotid gland cells. In some embodiments, the salivary gland cells comprise submandibular gland cells. The salivary gland cells may also be primary salivary gland epithelial cells, and may be mammalian cells, including rat cells. Advantageously, the inventors have discovered that salivary gland cells grown on silk fibroid scaffold retain properties of salivary gland cells in their native in vivo milieu. For example, in some embodiments, the salivary gland cells are arranged in three-dimensional cellular aggregates. In some embodiments, the salivary gland cells are globular in shape, in contrast to cells grown without SFS, which may be flat and round. In some embodiments, the salivary gland cells demonstrate a greater motility than those grown without SFS. In some embodiments, the salivary gland cells do not form a monolayer, in contrast to cells grown without silk fibroid scaffold. The salivary gland cells grown on SFS retain other morphological features of functional salivary gland tissue. For example, in some embodiments, the salivary gland cells comprise granule structures. In some embodiments, the granule structures have an average diameter of approximately 1 µm, which is consistent with morphology of salivary gland cells in vivo. In some embodiments, the granule structures occupy more than half of the cytosol of the salivary gland cells. These granule structures are consistent with being salivary secretory granules. In some embodiments, the salivary gland cells express β-adrenergic receptor on their cell surface, another hallmark of functional salivary gland cells. In some embodiments, the granule structures and/or the salivary gland cells themselves are capable of secreting amylase. As another indication that the salivary gland cells of the cell culture system of the present invention retain physiological functions of in vivo salivary gland cells, in some embodiments, the salivary gland cells are capable of secreting amylase in response to exposure to a β-adrenergic receptor agonist, which may be isoproterenol. In some embodiments, the salivary gland cells are capable of secreting amylase in response to exposure to isoproterenol at a concentration of $10^{-5}$ M for 30 minutes in PBS solution. Secretion of amylase may be measured by any method known by those of ordinary skill in the art. In particular, amylase enzymatic activity may be monitored. In some embodiments, the salivary gland cells are capable of secreting an amount of amylase sufficient to increase the amylase activity in the culture medium by at least a factor of 2 and/or at least a factor of 5 after exposure to isoproterenol as compared to amylase activity in the culture medium before exposure to isoproterenol. In some embodiments, the culture medium of the cell culture system comprises a β-adrenergic receptor agonist, including in some embodiments isoproterenol. In some embodiments, the culture medium comprises amylase secreted from the salivary gland cells. Another advantage of the present cell culture system is that in some embodiments the salivary gland cells retain the in vivo physiological property of being capable of constructing a three-dimensional extracellular matrix. This three-dimensional extracellular matrix is salivary gland-specific in some embodiments, which makes it useful in maintaining the physiological function of in vitro cultures salivary gland cells and in directing the differentiation of salivary gland cell progenitors, including pluripotent stem cells, into salivary gland cells. This can also be useful in generating salivary gland tissue, which can be used for therapy themselves or for testing of therapies in vitro. The three-dimensional extracellular matrix produced by the salivary gland cells of the present invention measures, in some embodiments, at least 5, 10, 15, 20, 25, 30, 35, 40, 45, 50, 60, 70, 80, 90, 100, 150, 200, 250, 300, 400, or 500 µm or more in each dimension, which has various advantages over matrices produced by cells that are not grown on silk fibroid scaffold. In some embodiments, the average height of the three-dimensional extracellular matrix measures between about 10 and 20 µm, 10 and 30 µm, 10 and 40 µm, 10 and 50 µm, 20 and 40 µm, 20 and 60 µm, 20 and 80 µm, 20 and 100 µm, 30 and 100 µm, 50 and 100 µm, 70 and 100 µm, 100 and 200 µm, 100 and 300 µm, 100 and 400 µm, 100 and 500 µm, or any range derivable therein. In some embodiments, the three-dimensional extracellular matrix comprises collagen type IV, which is a characteristic of matrices with in vivo physiological properties. As the salivary gland cells of some embodiments of the cell culture system are capable of producing a three-dimensional extracellular matrix, in some embodiments, the cell culture system comprises an extracellular matrix, which in some embodiments measures at least 5, 10, 15, 20, 25, 30, 35, 40, 45, 50, 60, 70, 80, 90, 100, 150, 200, 250, 300, 400, or 500 µm or more in each dimension. In some embodiments, the three-dimensional extracellular matrix comprises collagen type IV.

Also disclosed is a method of forming a salivary tissue-specific extracellular matrix comprising exposing the cell culture systems described above to ascorbic acid. A salivary tissue-specific extracellular matrix is an extracellular matrix with properties associated with the extracellular matrix found in salivary glands in vivo. In particular, a salivary tissue-specific extracellular matrix has the ability to support growth of salivary gland cells in such a way that the cells retain functional and morphological features of salivary gland cells in vivo. In some embodiments, a salivary tissue-specific extracellular matrix has the ability to induce, support, and/or help direct differentiation of salivary gland cell precursor cells to differentiate into salivary gland cells. In some embodiments, a salivary tissue-specific extracellular matrix has the ability to support growth of salivary tissue. Ascorbic acid can be used to induce salivary gland cells to produce a salivary tissue-specific extracellular matrix. In some embodiments, the method includes a step of incubating the cell culture system for a time and under conditions sufficient for the salivary gland cells to achieve confluence. Confluence is defined as a property of a cell culture wherein the cells cover substantially all of the growth surface. In some embodiments, the salivary gland cells reach only partial confluence, which means that only a portion of the growth surface is covered by salivary gland cells. For example, in some embodiments, the salivary gland cells reach at least 80 percent confluence, at least 85 percent confluence, at least 90 percent confluence, at least 95 percent confluence, or at least 99 percent confluence. In some embodiments, exposing the salivary gland cells to ascorbic acid is performed after the salivary glands achieve confluence. In some embodiments, confluence is substantially complete (e.g. 100 percent coverage of the growth surface) before exposure to ascorbic acid. In some embodiments, the salivary gland cells reach only partial confluence (for example, 80%, 85%, 90%, 95%, or 99% coverage of the growth surface). In some embodiments, the salivary gland cells are exposed to ascorbic acid for eight days. In some embodiments, the method of forming a salivary tissue-specific extracellular matrix further comprises decellularizing the extracellular matrix. Decellularizing means removing substantially all of the salivary gland cells. Decellularization is accomplished in some embodiments by incubating the salivary gland cells with a composition comprising Triton X-100 and $NH_4OH$. Also disclosed is the three-dimensional extracellular matrix produced by any of the methods described above.

Also disclosed is a three-dimensional extracellular matrix produced by salivary gland cells cultured on silk fibroid scaffold. In some embodiments, each dimension of the three-dimensional extracellular matrix measures at least 5, 10, 15, 20, 25, 30, 35, 40, 45, 50, 60, 70, 80, 90, 100, 150, 200, 250, 300, 400, or 500 µm or more. In some embodiments, the height of the three-dimensional extracellular matrix measures between about 100 and 200 µm, 150 and 250 µm, 200 and 300 µm, 250 and 350 µm, or 300 and 400 µm. In some embodiments, the extracellular matrix is essentially free of salivary gland cells. Salivary gland cells can be removed from the extracellular matrix by any method known to those of skill in the art. For example, the salivary gland cells can be removed by incubating with a composition comprising Triton X-100 and $NH_4OH$. In some embodiments, the silk fibroid scaffold is coated with fibronectin.

Also disclosed is a method of producing salivary gland cells, the method comprising incubating precursors of salivary gland cells with any of the three-dimensional extracellular matrices described above. In some embodiments, the three-dimensional extracellular matrices of the present invention have the ability to support, induce, and/or direct the growth of salivary gland cells from salivary gland precursors. In some embodiments, incubating the precursors with the three-dimensional extracellular matrices can include plating the precursor cells on a surface comprising a three-dimensional extracellular matrix and maintaining growth and nutrient conditions sufficient to allow growth and/or differentiation. In some embodiments, the salivary gland cells are pluripotent stem cells, including in some embodiments, mesenchymal stem cells and/or cells derived from bone marrow and/or umbilical cord. Also disclosed is a method of treating a salivary gland condition in a subject comprising providing to the subject the salivary gland cells produced by any of the methods described herein. The salivary gland cells can be provided to the subject in any way known by those of skill in the art, including, for example, implantation and/or injection.

Also disclosed is a method of differentiating cells comprising incubating cells with any of the three-dimensional extracellular matrices described above.

Also disclosed is a method of producing salivary gland tissue comprising obtaining salivary gland cells or salivary gland precursor cells and incubating the salivary gland cells or salivary gland precursor cells with any of the three-dimensional extracellular matrices described above. In some embodiments, the salivary gland precursor cells are pluripotent stem cells, including mesenchymal stem cells. In some embodiments, the pluripotent stem cells are derived from bone marrow or umbilical cord. Tissues produced by this method may be useful in a variety of ways. In some embodiments, there is disclosed a method of treating a salivary gland condition in a subject comprising providing to the subject the salivary gland tissue produced by any the methods described herein. Tissues produced according to the methods described herein may also be useful in testing potential therapeutics or in determining the biological function or result of a particular substance or condition.

Tissues produced in vitro yet retaining physiological features of in vivo tissues provide a particularly useful tool for monitoring the effects of proposed therapies or molecules on the physiological functions of the tissues. Accordingly, there is disclosed a method of testing the biological activity of a substance comprising obtaining any of the cell culture systems described above; adding the substance to the cell culture system; and measuring a parameter of the cell culture system to determine the effect of adding the substance to the cell culture system. Adding the substance to the cell culture system may comprise adding the substance to the culture medium. The culture medium may be exchanged for a culture medium comprising a particular substance or combination of substances to monitor the effects of the culture medium change on the physiological functions of the salivary gland cells. Measuring a parameter of the cell culture system may include, for example, observing growth rates or morphological features of cells. It may also include, for example, measuring the ability of the salivary gland cells to secrete amylase or other substances. Any biologically relevant parameter may be measured and monitored to determine the biological effect of exposing the cells to a substance or of changing any conditions of growth. Changes in the parameter being measured or monitored can be attributed to the presence of the substance or the change in growth conditions if a corresponding control does not show the same change. In some embodiments, the substance being tested is a candidate therapeutic to treat a condition, including, for example, disorders of the salivary gland or an oral disease. In some embodiments, the condition is Sjögren's syndrome, diabetes, a renal disease, or a side effect of a xerostomic medication or radiotherapy.

There is also disclosed a method of testing the biological activity of a substance comprising obtaining the extracellular matrix of any of claims 39 to 42; incubating salivary gland cells or salivary gland precursor cells with the extracellular matrix; contacting the salivary gland cells or salivary gland precursor cells with the substance; and measuring an activity or property of the salivary gland cells or salivary gland precursor cells to determine the effect of contacting the salivary gland cells or salivary gland precursor cells with the substance. In some embodiments, the substance is a candidate therapeutic to treat a condition. In some embodiments, the condition is an oral disease or a disorder of the salivary glands. In some embodiments, the substance is a cellular growth factor or cellular differentiation factor.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present inventors examined the behavior of and extracellular matrix produced by salivary gland epithelial cells grown on silk fibroin scaffold (SFS) versus regular tissue culture plastic (TCP). The inventors discovered that the SFS culture system closely resembles the in vivo situation for retaining the salivary acinar and promoting the synthesis of salivary tissue-specific ECM. The silk in the SFS is a natural product from Bombyx Mori cocoon that consists of two major protein classes, fibroins and sericins (Leal-Egana & Scheibel, 2010). Since sericins have been identified as allergens in human, the fibroin silk after removing sericins is usually used as scaffolds. The fibroin silk scaffold is a favorite material for tissue engineering as compared to the other materials due to its flexible elasticity, easy nutrition supply (adequate pore sizes), poor surface for microorganism adherence, low toxicity/immunogenicity, and biodegradability (Leal-Egana & Scheibel, 2010).

The inventors have discovered that the SFS culture system provides a physiological environment for faithfully retaining the features of salivary secretory cells and promoting the synthesis of salivary tissue-specific ECM. Compared with 2D culture system, it much better mimic in vivo for studying the behavior of salivary gland epithelial cells in response to the variety of treatments, including new drug testing or radio- and chemo-therapeutic testing. Importantly, the cellular and ECM organizations of the pSGECs on SFS was close to that observed in the native salivary gland secretory tissues (D'Avola, et al., 2006). This cell culture system will be useful in the establishment of tissue-specific microenvironment or niches for repairing or even reconstructing functional salivary gland tissues.

Through immunostaining confocal microscopy and phase contrast microscopy, the inventors have demonstrated that collagen IV, a major composition of basement membrane, is indeed present in the ECM of pSGECs grown on SFS with much more intense expression surrounding 3-D aggregates than in the 2-D TCP culture. The results showed SFS likely facilitates pSGECs to generate the basement membrane proteins in a 3D structure resembling acini in the native salivary gland (D'Avola, et al., 2006). The inventors have demonstrated that salivary pSGECs have the potential to synthesize salivary gland microenvironment for future tissue engineering using multipotent stem cell differentiation into functional salivary gland epithelial cells in vitro and/or in vivo.

Figures 8A, 8B, 8C, 8D, 8E, 8F, 8G, 8H:
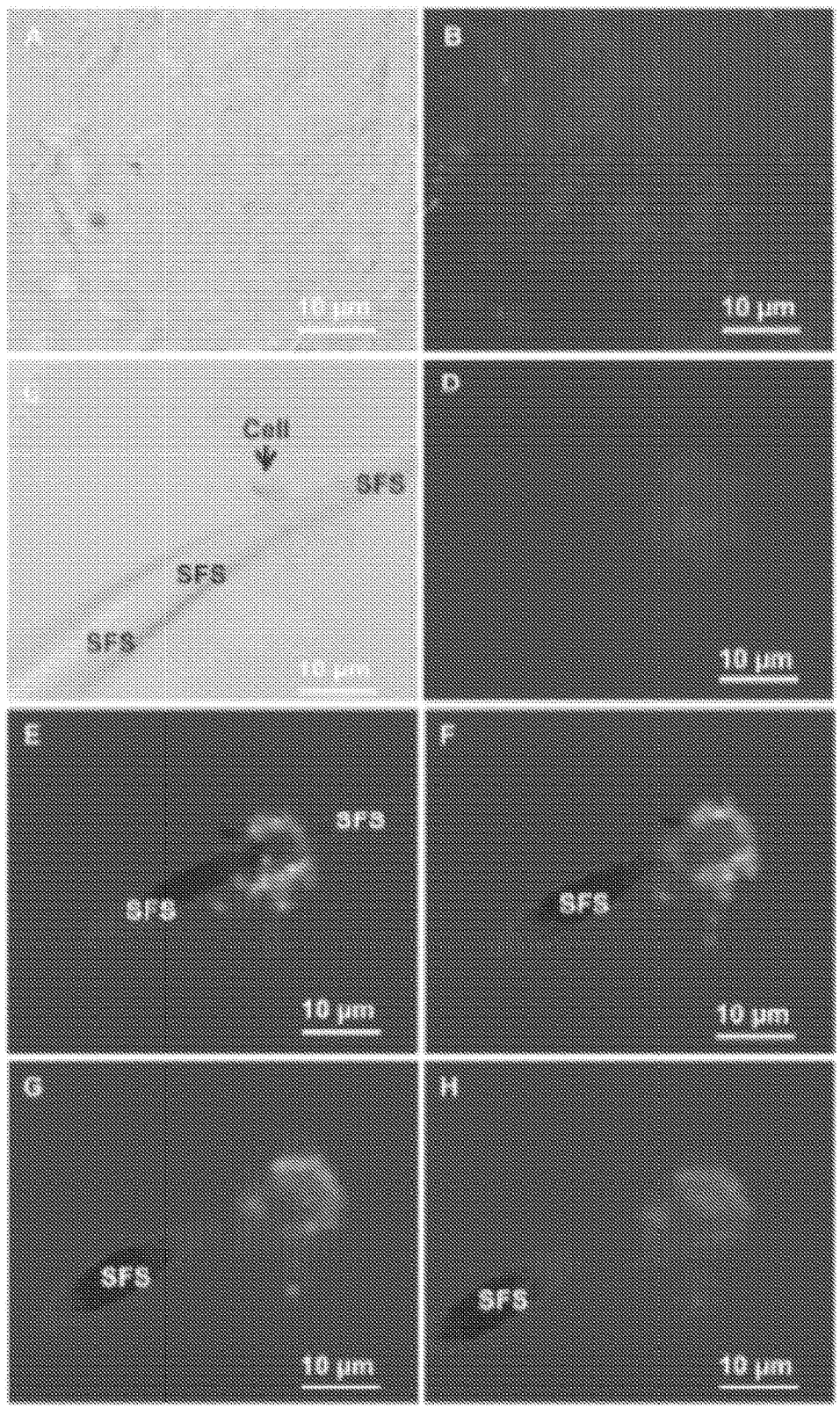
FIG. 8A-8H—Localization of type IV collagen produced by primary submandibular (SM) gland epithelial cells cultured on tissue culture plastic (TCP) and silk fibroin scaffolds (SFS). SM gland epithelial cells were grown for 5 weeks as described in the Methods and then fixed for phase contrast microscopy and localization of type IV collagen by confocal microscopy. Images in panels A and C are phase contrast images of cells grown on TCP and SFS, respectively. Panel B is an immunofluorescent image of cells cultured on TCP and stained with antibody to type IV collagen; note the lack of staining under these culture conditions. Panels D through H are a confocal microscopy z-scan series (viewed in 3 μm sections, bottom to top) of SM gland epithelial cell aggregates growing on and surrounding the SFS fiber (blue fluorescence in original). Most notably, these cells are producing high levels of type IV collagen (green fluorescence in original).
Figure 9:
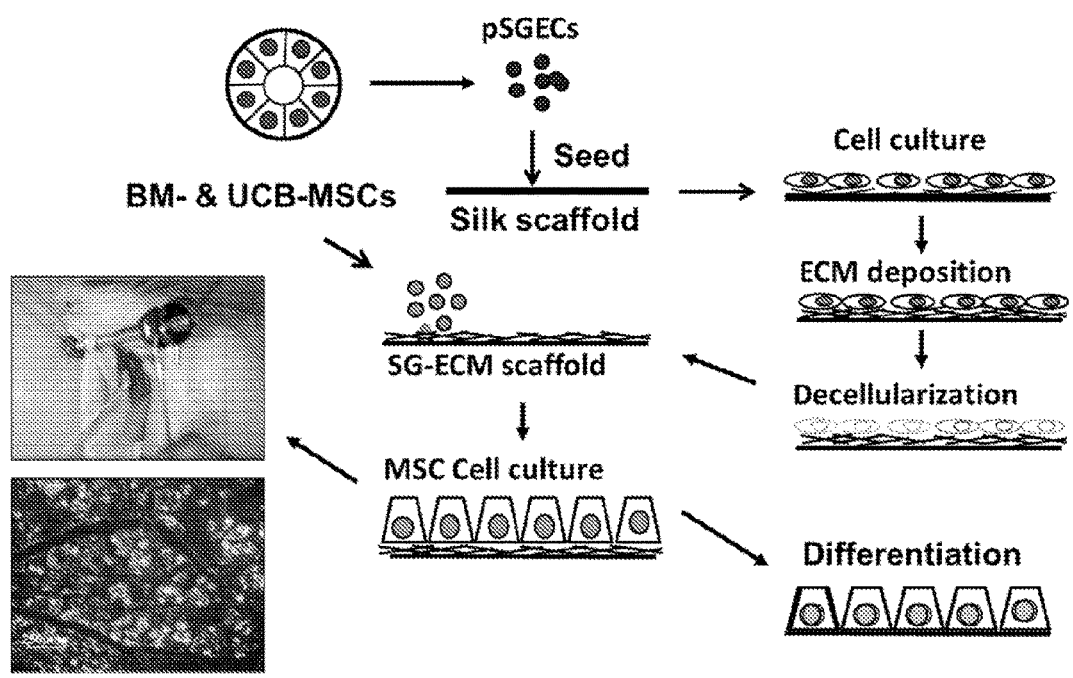
FIG. 9—Development and characterization of a 3D salivary gland-derived ECM scaffold, which provides a unique microenvironment for directing multipoint bone marrow (BM) or human umbilical cord blood (UCB)-derived mesenchymal stem cells (MSCs) differentiation into a salivary gland epithelial cell lineage and enhancing these cells to form the functional salivary gland tissue. Tissue-specific ECM derived from cultured salivary gland epithelial cells (SG-ECM) on a silk fibroin scaffold (SFS) were developed. The primary salivary cells grown on SFS retain the important functional and structural features of salivary glands and produce an extracellular matrix network mimicking native salivary gland cell niches.

SFS not only keeps pSGECs in differentiated stages in long term culture, but also allows pSGECs to form a 3-D ECM structure. Using the decellularization procedures with minimal disturbances to the structure of the ECM (Crapo, et al., 2011), the SEM and TEM revealed that pSGECs were able to produce extensive ECM on the surface of SFS. Strikingly, the morphological features of ECM network on TEM mimic the decellularized rat salivary gland tissue (D'Avola, et al., 2006), suggesting that pSGECs can produce a native salivary specific 3D-ECM in vitro. While the amount of ECM produced by cells are visually different between the 2D and 3D cultures, the composition of the ECM under the two culture conditions was, based on immunofluorescent staining, different as well (FIG. 8). The cell culture system disclosed herein may also be used to study the differences between the two ECMs.

The inventors have discovered that pSGECs from rat parotid or submandibular glands grown on SFS retained more differentiated features of salivary acinar cells as compared to culture of these cells on TCP. The pSGECs cultured on SFS formed clusters maintained differentiated status as in the native organ (salivary gland). Strikingly, pSGECs grown on SFS retained their secretory status by exhibiting secretory granule-like structures in cell surface and in cytosol. In contrast, the morphology of pSGECs grown on TCP was shown in round and flat without secretory function. The detection of mucins in SM gland epithelial cells, but not PG epithelial cells, further highlights the unique ability of SFS to promote maintenance of the differentiation state of pSGECs. At the resting condition, the pSGECs of parotid and submandibular glands on SFS consecutively secrete amylase into culture media. Furthermore, pSGECs of parotid gland on SFS maintained sensitivity to amylase secretion in response to isoproterenol treatment, suggesting functional β-adrenergic receptors on these cells. Interestingly, the submandibular gland pSGECs do not have isoproterenol induced amylase release (FIG. 6). These results are well consistent with previous studies indicating that isoproterenol has differentiated effects on amylase secretion in rat parotid and submandibular gland cells, i.e., β-adrenergic receptor stimulated amylase secretion only occurs in the rat parotid gland cells/tissues whereas amylase secretion by rat submandibular gland cells/tissue is constitutive with no response to β-adrenergic receptor regulation (Busch, et al., 2002). These results demonstrate that SFS has potential as a scaffold for creating the salivary gland cell niche in vitro and may provide an approach for inducing multipotent stem cells to provide therapeutically meaningful numbers of salivary gland progenitor cells for regenerating these tissues in patients.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Preparation of the Silk Scaffolds:

The three dimensional (3-D) silk fibroin scaffolds (SFS) were prepared based on a previously described technique (Sofia, et al., 2001). Briefly, silk cocoons from *Bombyx Mori* (Paradise Fibers, Spokane, Wash.) were boiled in aqueous 0.02M $Na_2CO_3$ and 0.3% (w/v) ivory soap for 1 h to remove sericin from the silk fibroin. Cocoons were then rinsed thoroughly with deionized (DI) water to remove any trace of soap and impurity. The silk fibers were dissolved in 9.5M LiBr solution for 30 minutes at 50° C., yielding a 10% weight/volume solution. Next, the liquid silk/LiBr solution was dialyzed for 3 days (2 kDa molecular cut off dialysis membranes, Thermo Scientific Pierce, Rockford, Ill.) in running DI water. The resulting aqueous solution was lyophilized for 48 hrs (LabConco LC-CE-7753522, Kansas City, Mo.). Samples were then rehydrated in water yielding a 5% (w/v) solution which was sonicated for 2 min. 50 µl of liquid silk were casted onto Teflon® molds (5 mm diameter) creating a thin film. The entire mold setup was then placed in the freezer and lyophilized again. Silk structure was submerged in methanol for 10 min to allow for structural change from α-helix to β-sheet. This step made the films insoluble in cell culture media. The methanol was then removed and the films were washed repeatedly in distilled water. The silk films were sterilized using an Ethylene Oxide (AN74i Anprolene gas sterilizer, Andersen Sterilizers, Inc) treatment for 12 hrs. Prior studies have shown that ethylene oxide sterilization did not alter the physical properties of the SFS (Siritientong, et al., 2011; de Moraes, et al., 2014).

Preparation of Primary Cells from Parotid and Submandibular Glands.

Salivary primary epithelial cells (pSGECs) from parotid and submandiblar glands were prepared from 3-month old male Sprague-Dawley rats following the procedure described previously by us (Yeh, et al., 1991). Briefly, parotid and submandibular glands were dissected, finely minced and digested with collagenase (96 U/ml, Wathington Biochemical Corp, Lakewood, N.J.) and hyaluronidase (0.19 mg/ml, Sigma) in Hank's balance salt solution containing 33 mM HEPES, pH 7.4 (HBSS) at 37° C. for 60 min with vigorous agitation of 300 rpm. During the process, the digestive mixture was oxygenated every 10 min. At the end, the digestive mixture was passed through a 100 (for parotid) or 40 (for submandibular gland) µm nylon cell strainer and the cells were collected and washed with HBSS by centrifugation at 100 g for 5 min. The freshly isolated salivary gland cells were cultured for four weeks in DMEM/F12 medium (1:1 ratio) containing 1.1 mM hydrocortisone, 15% selected fetal bovine serum (sFBS) and antibiotic-antimycotic until near confluent (about four weeks). Previous studies have indicated the primary cells prepared by this method were 90% secretory (acinar-like) cells (Fujita-Yoshigaki, et al., 2005). The cultured cells were harvested using trypsin/EDTA and then used for the experiments (see below).

Cultures of Salivary Gland Cells on 2-D TCP or 3-D SFS.

TCP and SFS were pre-coated with human fibronectin. One milliliter of 16.7 µg/ml fibronectin (Millipore) in phosphate buffered saline (PBS) was added to each well of 6-well plate or onto SFS and incubated for 1 hour at 37° C. After rinsing with PBS, the pSGECs were seeded on the coated TCP disks or SFS and grown in a F12/DMEM (1:1 ratio) media containing 1.1 mM hydrocortisone, 15% sFBS and antibiotic-antimycotic at 37° C. in a humidified 5% $CO_2$/95% air incubator for 4 or 5 weeks. The media was refreshed every three days. In the last week the media was supplemented with ascorbic acid (50 µM) to promote extracellular matrix (ECM) formation. The last refreshment media were collected for amylase analysis.

After the culture period, the 2-D TCP and 3-D SFS cultures were subjected to further morphological, functional and biochemical studies. Some of the TCP and SFS cultures were decellularized according to our previous published method (Chen, et al., 2007). In brief, the cultures were extensively washing with PBS and cells were removed by incubation with 0.5% Triton X-100 containing 20 mM NH4OH in PBS for 5 min at room temperature. The salivary cell produced ECM on the SFS and TCP surface was evaluated with scanning electron microscopy (SEM).

Cell attachment and proliferation was determined with the AlamarBlue assay according to the manufacturer's instructions (Invitrogen, Grand Island, N.Y.) (Widhe, et al., 2010; Mauney, et al., 2007). Cell growth was assessed every other day by incubation of the cultures with the AlamarBlue reagent (1:10 dilution) for 4 h at 37° C. After incubation, 100 µl of the culture media were transferred to a 96 well plate and fluorescence measured using a Spectromax M2 microplate reader (Molecular Devices, Sunnyvale, Calif.) with an excitation wavelength of 560 nm and an emission wavelength of 590 nm.

Histology and Electron Microscopy.

For histology, SFS, after being cultured with parotid or submandibular gland epithelial cells, were washed with PBS, fixed with 10% neutral buffered formalin (Sigma Aldrich, St. Louis, Mo.) overnight, and then embedded in paraffin for light microscopy. Scaffolds were sectioned and stained with hematoxylin and eosin (H&E), periodic acid-Schiff (PAS) (detects polysaccharides and mucosubstances such as glycoproteins, glycolipids) or Alcian blue (detects mucins) (Sarosiek, et al., 1994) for viewing of the cells and their morphology and the SFS.

For electron microscopy, cultures on TCP and SFS were washed 3 times with PBS and fixed with 2% glutaraldehyde in 0.1M sodium cacodylate buffer (pH 7.2) for 1 h and then transferred to 0.1M cacodylate buffer solution. The specimens were dehydrated in ascending concentrations of ethanol (from 70% to 100%). After dehydration, the TCP and SFS specimens were attached to a stub and sputtered-coated with gold-palladium for scanning electron microscopy (SEM). The specimens were examined using an EVO-50EP SEM manufactured by Carl-Zeiss SMT.

For transmission electron microscopy (TEM), the cell cultures were fixed as above and embedded in epoxy resin. Ultrathin sections were stained with uranyl acetate and lead citrate and examined using a Joel 1230 electron microscope (Loel Ltd., Tokyo, Japan).

Measurement of α-Amylase Activity.

The α-amylase activity in culture media was assessed as an indicator for the secretory functions of cultured salivary gland cells using the EnzChek Ultra Amylase Assay Kit (Invitrogen) according to the manufacturer's instruction. The amylase activities were analyzed under both stimulated and non-stimulated conditions. To assess amylase secretion in non-stimulated cells, the media was collected after salivary gland cells were grown for four or five weeks. The protein concentrations were measured with Bio-rad using bovine serum albumin as standards. Amylase activities were monitored by the increase of fluorescence excited at 495 nm and emitted at 515 nm following digestion of the DQ™ starch substrate and relief of quenched fluorescence using a SpectraMax M2 microplate reader (Molecular Device).

To measure the amylase secretion in response to β-adrenergic receptor stimulation, the cells cultures were washed with PBS containing $MgCl_2$ (1 mM) and $CaCl_2$ (1 mM) (PBS solution) at room temperature. The cells were then incubated in PBS solution at 37° C. for 30 min to assess the basal amylase secretion. Subsequently, these cells were exposed to 10 µM isoproterenol at 37° C. for 5 or 30 min in the PBS solution. The amylase activities and protein concentrations in the solution were measured as described above.

Immunofluorescence of Collagen IV.

The expression of basement membrane collagen IV on TCP and SFS cultures was examined with immunofluorescence following the procedures previously described (Zhang, et al., 2008). Briefly, cells grown and attached on TCP and SFS were fixed with 4% paraformaldehyde and permeabilized with 40 µg/ml digitonin in PBS for 30 min at room temperature. The permeabilized cells were incubated with 10% fetal bovine serum in PBS for 60 min and subsequently hybridized with or without rabbit polyclonal IgG anti-type IV collagen (1:50 dilution in PBS containing 2% FBS, 0.01% Triton X-100; Santa Cruz Biotechnology) at 4° C. overnight. The cells were washed with PBS containing 0.1% Tween 20 and incubated with Alexa 488-labeled goat anti-rabbit IgG (1:1000 dilution; Invitrogen) for 1 h at room temperature. Some specimens were counter stained with DAPI as indicated. Labeled cells were washed, and images were acquired using an Olympus confocal laser scan imaging system with excitation/emission wavelengths of 405/450 nm for nuclei and 488/554 nm for type IV collagen.

Statistical Analysis.

All data are presented as the mean±standard deviation. Statistical analysis of the experimental data was performed using Student's t test with significance at $p<0.05$. Each experiment was repeated a minimum of three times with an n=4 for each treatment group.

Example 2—Results

Figure 1:
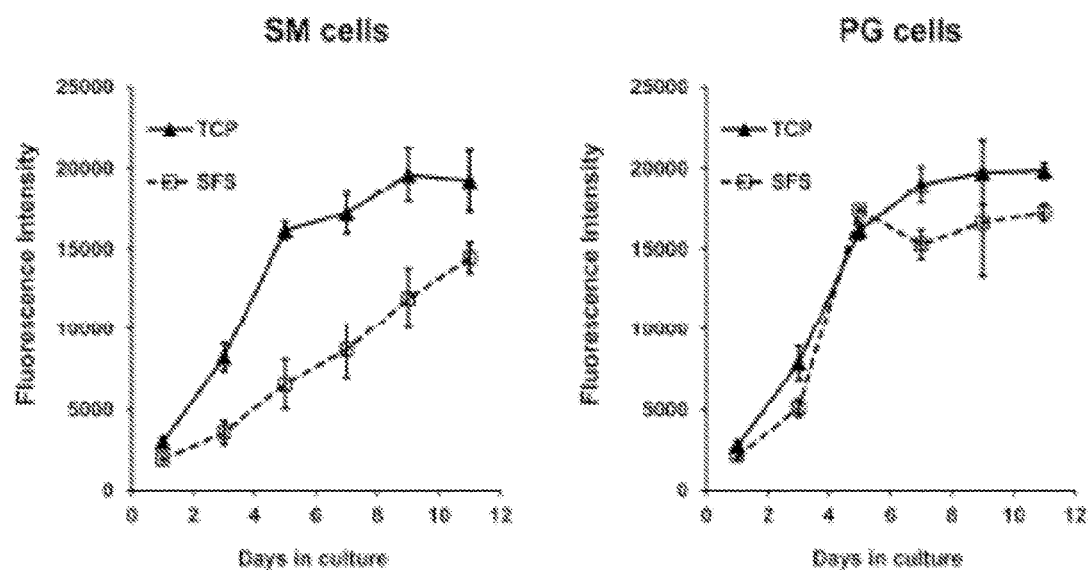
FIG. 1—Attachment and proliferation of primary salivary gland epithelial cells (pSGECs) on tissue culture plastic (TCP) and silk fibroin scaffolds (SFS) were assessed using AlamarBlue. Rat submandibular (SM, left panel) and parotid (PG, right panel) gland primary epithelial cells were cultured for up to 12 days on SFS or TCP. The change in cell number was assessed with AlamarBlue at the indicated times. The data shown in the graphs are from one representative experiment (mean±SD fluorescence intensity; n=4 wells).

Primary salivary gland epithelial cells (pSGECs) attached and proliferated on both TCP and SFS. Cell attachment and proliferation were assessed during culture by use of the AlamarBlue assay (Fujita-Yoshigaki, et al. 2005). The initial number of submandibular (SM) or parotid (PG) gland epithelial cells attached to SFS was the same as that for TCP (FIG. 1). Further, the proliferative pattern displayed by PG epithelial cells when grown on both TCP and SFS were very similar over 12 days in culture (FIG. 1). In contrast, the proliferation of SM gland epithelial cells cultured on TCP plateaued around day 6, indicating that the cells had reached confluence, while cells cultured on SFS continued to proliferate during the entire culture period, suggesting that cell confluence was delayed (FIG. 1).

Primary Salivary Gland Epithelial Cells on SFS, but not TCP, Maintained Secretory Features In Vitro.

pSGECs obtained from rat parotid (PG) or submandibular (SM) glands were cultured either TCP or SFS in growth media for 3 or 4 weeks, followed by incubating in ECM promoting media supplemented with ascorbic acid (50 µM) for an additional 8 days. The cultures were then processed for examination by light microscopy, SEM, or TEM.

Figures 2A, 2B, 2C, 2D, 2E, 2F, 2G, 2H, 2I:
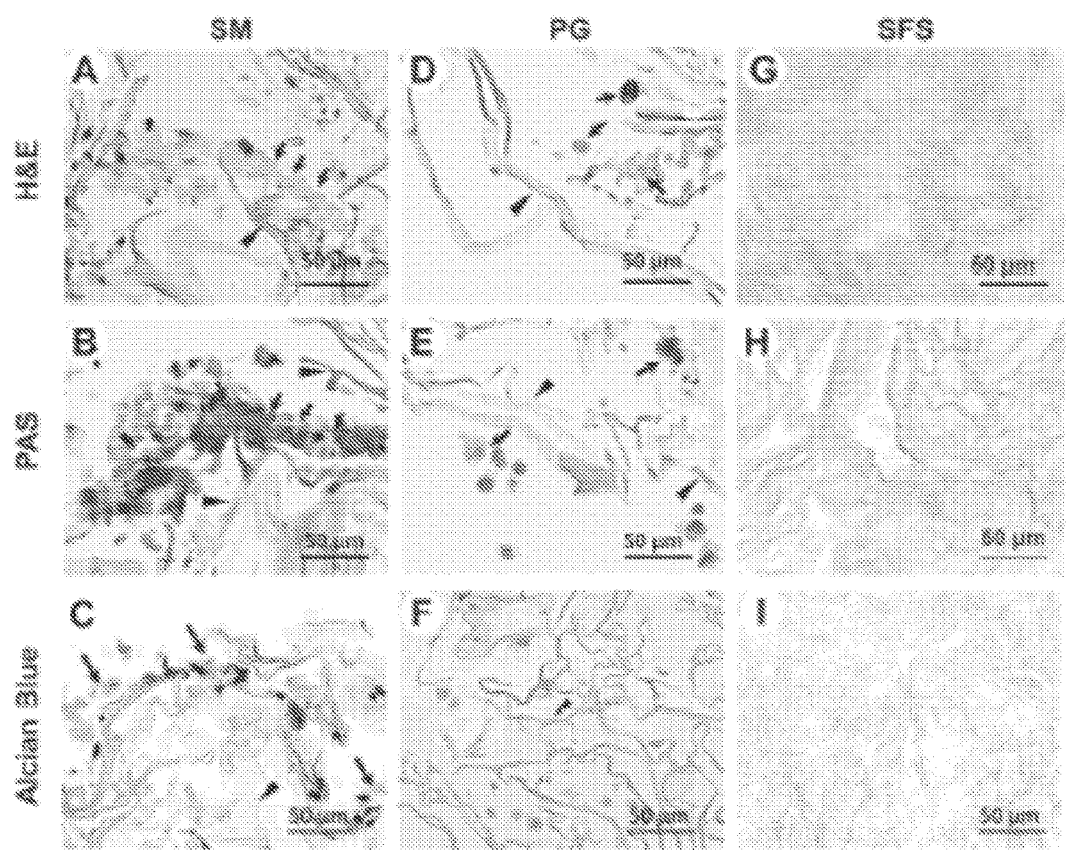
FIG. 2A-2I—Histological staining of pSGECs grown on silk fibroin scaffolds (SFS). Rat submandibular (SM, A-C) and parotid (PG, D-F) gland epithelial cells cultured on SFS were sectioned and stained with hematoxylin and eosin (H&E, A & D), periodic acid—Schiff (PAS, B & E), or Alcian blue (C & F) as described in the Methods. The SFS without cells served as controls (G, H & I). Cell aggregates (solid black arrows in A and D) were observed in H&E stained sections from both SM and PG cultures. In addition, cells from both tissues were PAS positive (solid black arrows in B and E). Alcian blue staining, indicative of mucin production, was found in SM cultures (solid black arrows in C), but not in PG cultures (F). Solid arrow heads identify SFS in these micrographs.

By use of bright field microscopy, pSGECs grown on SFS displayed features of salivary gland acinar cells (FIG. 2). Staining with H&E and PAS (indicative of polysaccharides and mucosubstances such as glycoproteins, glycolipids) revealed the presence of aggregated cells associated with the silk fibers. In the majority of the cells, the cytosol contained glycoprotein-rich secretory granules and nuclei located near the cell membrane. In sections stained with Alcian blue, mucin-like substances were found in SM gland epithelial cells but not PG epithelial cells.

Figures 3A, 3B, 3C, 3D, 3E, 3F, 3G, 3H:
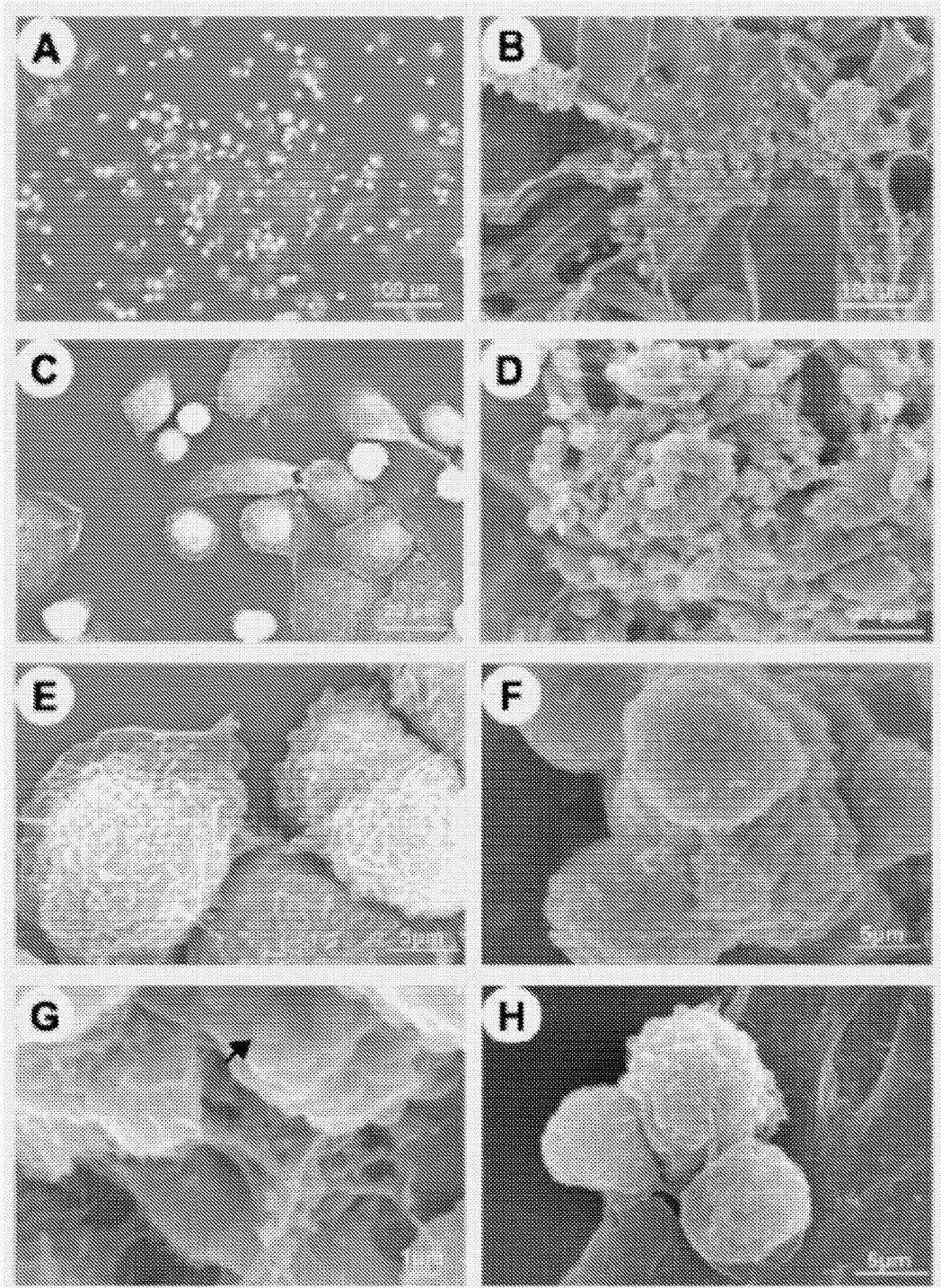
FIG. 3A-3H—Scanning electron micrographs of primary salivary gland epithelial cells (pSGECs) grown on tissue culture plastic (TCP) or silk fibroin scaffolds (SFS). Submandibular (SM) gland epithelial cells were cultured on TCP (A, C, E) or SFS (B, D, F, G) for 5 weeks and then viewed in the scanning electron microscope (SEM) as described in the Methods. With increasing magnification, different morphological features of the cells growing on the 2 culture surfaces could be clearly discerned (TCP: A, C, E; SFS: B, D, F, G). SM gland epithelial cells grown on SFS displayed secretory granule-like structures that could be clearly seen at high magnification (black arrow in G). The micrograph in H shows that PG epithelial cells grown on SFS; at the same magnification as the SM cells (see F), have remarkably similar surface morphologies.

SEM further revealed that SM gland epithelial cells grown on TCP were mainly round and flat (FIGS. 3 A & C), while those cultured on SFS formed 3-D cell aggregates/clusters (FIGS. 3 B & D). At a higher magnification, cells maintained on TCP displayed numerous projections from the cell surface (FIG. 3E), whereas secretory granule-like structures were only observed on the surface of cells cultured on SFS (FIGS. 3 F & G). The diameter of these granule-like structures was approximately 1 µm, which is consistent with the size of salivary gland secretory granules of acinar cells in vivo (D'Avola, et al., 2006). Similar granule-like structures were also observed in PG epithelial cells grown on SFS (FIG. 3H).

Figures 4A, 4B, 4C, 4D:
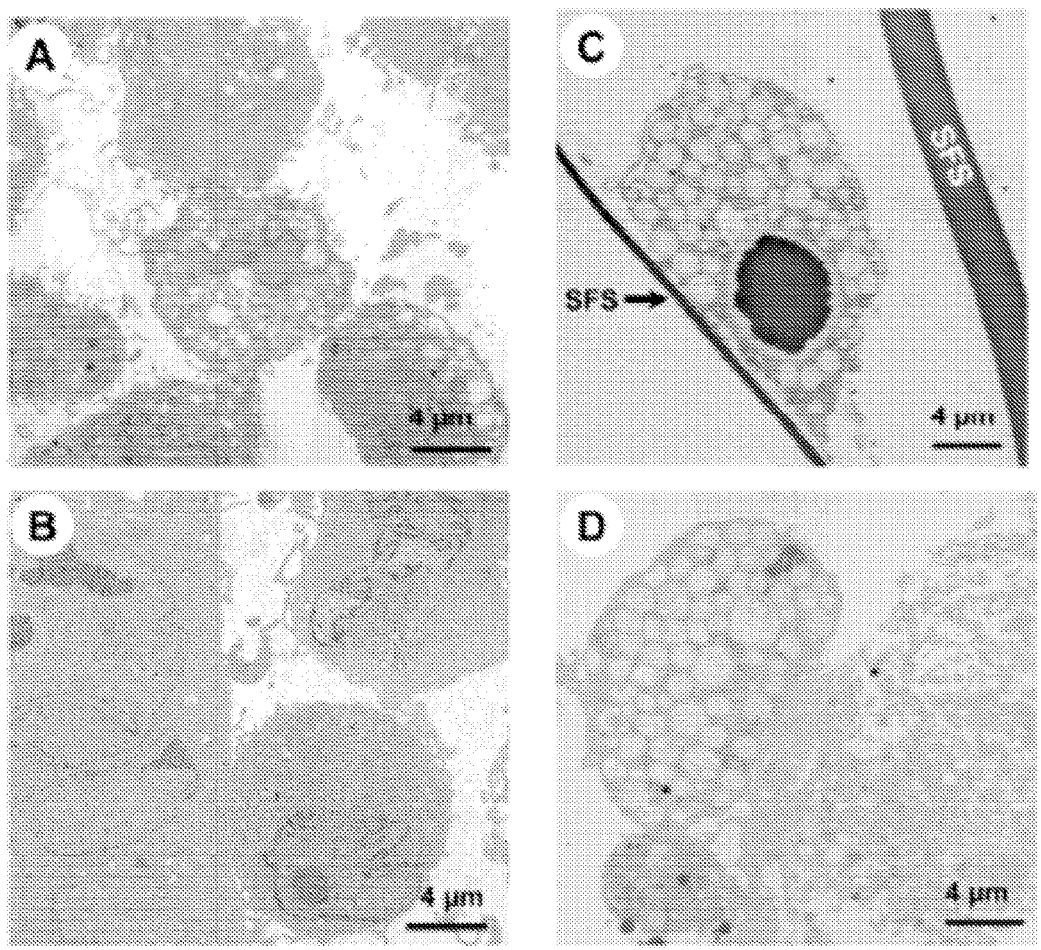
FIG. 4A-4D—Transmission electron micrographs of primary salivary gland epithelial cells (pSGECs) grown on tissue culture plastic (TCP) or silk fibroin scaffolds (SFS). Cells were cultured on TCP (A, B) or SFS (C, D) for 5 weeks and then viewed in the transmission electron microscope (TEM) as described in the Methods. The micrographs (A, B) on the left show submandibular (SM) gland epithelial cells grown on TCP; no secretory granule-like structures are observed in these cells. In contrast, SM gland epithelial cells cultured on SFS display prominent secretory granules (C, D).

Using TEM, the ultrastructure of these secretory granule-like structures was further revealed in cross section and it was found that they occupied the majority of the cytosol in cultures on SFS (FIGS. 4C & D). In contrast, cells cultured on TCP contained very few secretory granules and the ones that were present appeared moderately to severely atrophic (FIGS. 4A & B).

Figure 5:
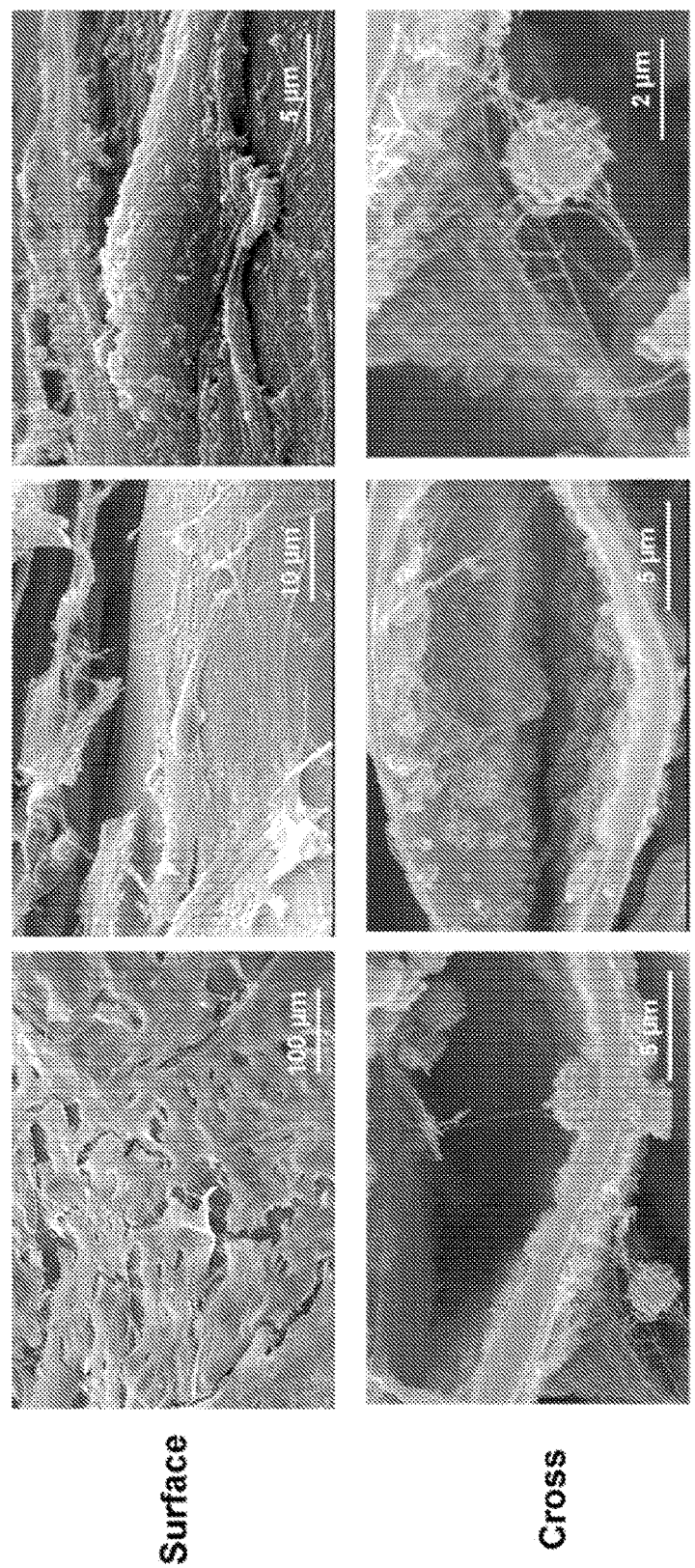
FIG. 5—SEM images of hBMSCs culture on SFS.

To demonstrate whether SFS provides a special environment to retain tissue-specific cellular organization, parallel experiments were performed with human bone marrow stromal cells (hBMSCs, passage 3) cultured on SFS. SEM revealed that hBMSCs, unlike salivary epithelial cells, were only lined on the surface of SFS forming a monolayer (FIG. 5). Moreover, hBMSCs cultured on SFS had many folds of plasma membrane that project from their surface as well as the cellular processes for cell-to-cell connections as compared to these cells grown on TCP (Chen, et al., 2007).

pSGECs Cultured on SFS, but not TCP, Maintained their Secretory Function In Vitro.

Figures 6A, 6B, 6C:
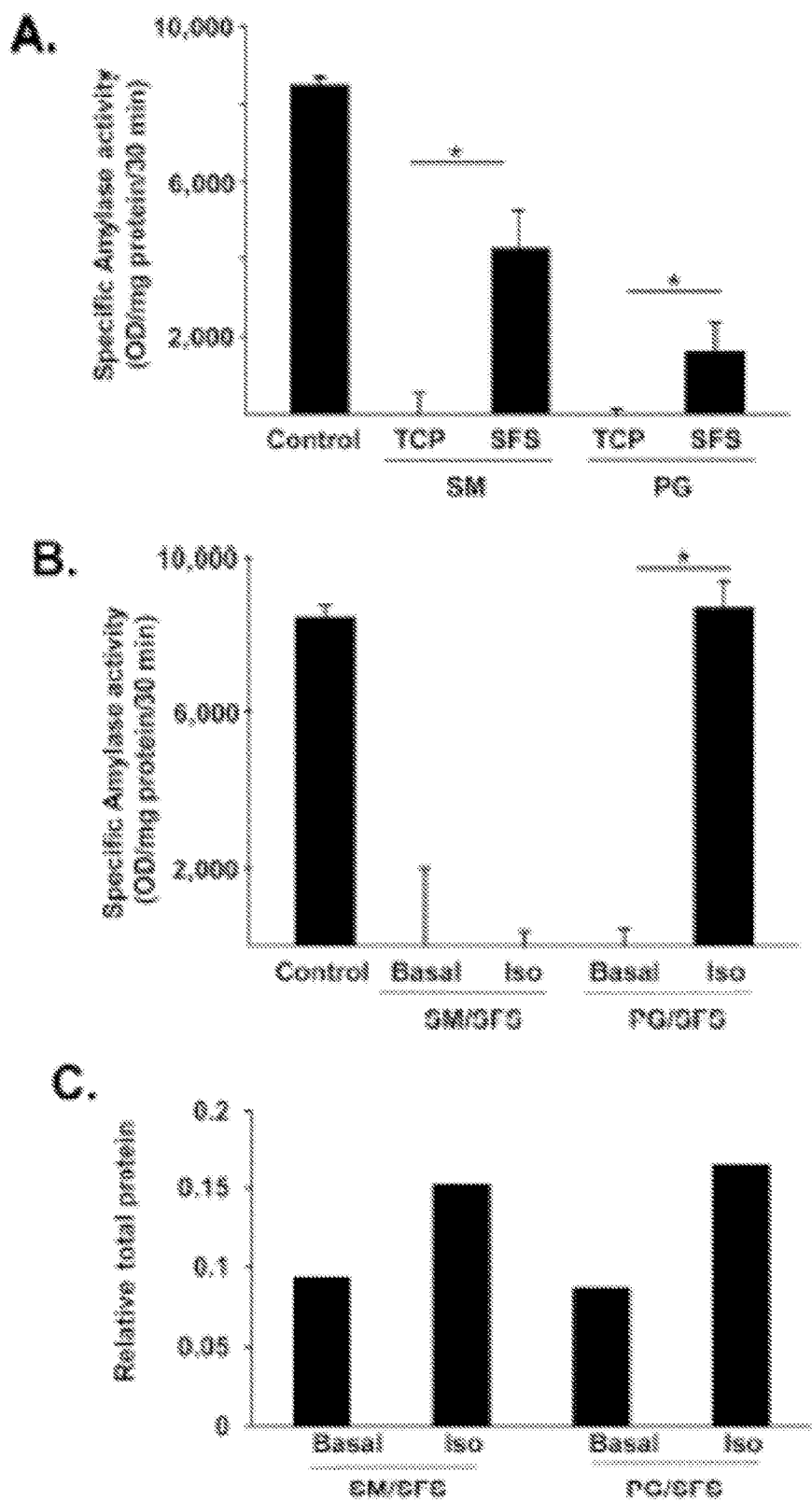
FIG. 6A-6C—Amylase and protein secretion by primary salivary gland epithelial cells (pSGECs) grown on tissue culture plastic (TCP) and silk fibroin scaffolds (SFS). Rat submandibular (SM) and parotid (PG) gland epithelial cells were cultured on TCP or SFS for 5 weeks in growth media as described in the Methods. Amylase activity (A and B), released by the cells, was measured as described in the Methods. Values shown in the graphs (A and B) represent the mean±SD for amylase specific activity. Panel A shows enzyme activity released into the media. Panel B shows the enzyme activity released in response to treatment with isoproterenol ($10^{-5}$ M, 30 min at 37° C.) (see Methods for details). Mouse saliva was used as a positive control for amylase activity. Representative data from one of two independent experiments are shown; each experiment was run in triplicate (n=3). The values in panel C represent total protein released by cells untreated or treated with isoproterenol ($10^{-5}$ M, 30 min at 37° C.) from a typical experiment (see Methods for details). *$p<0.05$, TCP vs. SFS (Panel A) or Basal vs Iso treatment (Panel B).

The secretory function of pSGECs cultured on TCP and SFS was first assessed by measuring amylase release into the culture media. There was a remarkable amount of enzyme produced by cultures of SM and PG epithelial cells grown on SFS, but not TCP (FIG. 6A). To further evaluate the secretory function of pSGECs grown on SFS, amylase release in response to β-adrenergic receptor stimulation, the receptor responsible for a major amount of salivary protein secretion (Baum, et al., 1993), was examined. When PG epithelial cells cultured on SFS were treated with isoproterenol ($10^{-5}$ M for 30 min in PBS solution), amylase activity increased sharply over basal levels (5.3 fold; FIG. 6B), indicating responsiveness to this agonist. In contrast, amylase production by SM gland epithelial cells did not respond to isoproterenol stimulation, in agreement with a previous study (Busch, et al., 2002). Notably, these differences in measurable activity and response to agonist treatment were not due to differences in total protein production (FIG. 6C).

SFS Facilitated pSGECs to Produce a Tissue-Specific ECM.

Figures 7A, 7B, 7C, 7D, 7E, 7F:
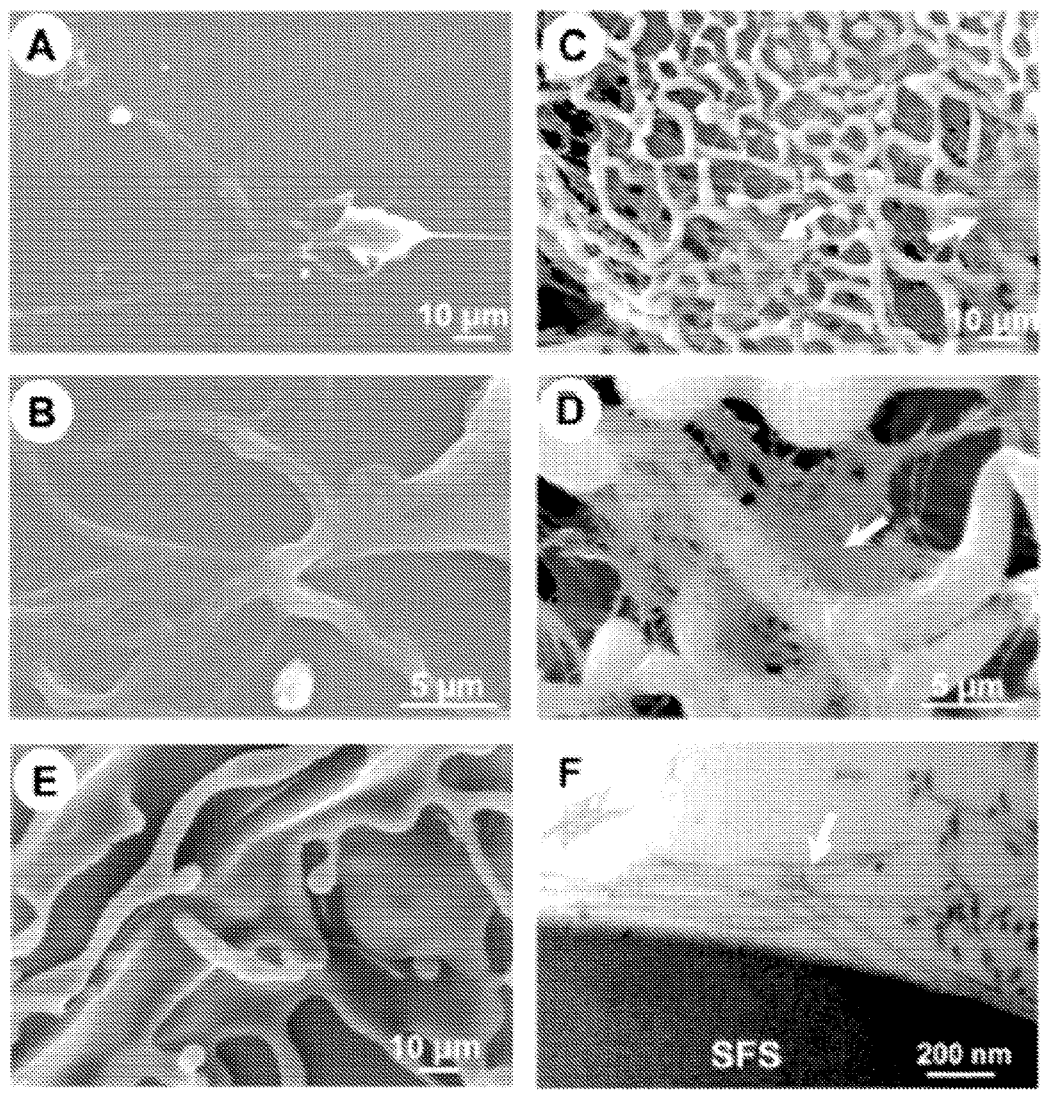
FIG. 7A-7F—Scanning- and transmission electron micrographs of extracellular matrix (ECM) produced by primary submandibular (SM) gland epithelial cells grown on tissue culture plastic (TCP) and silk fibroin scaffolds (SFS). The cells were cultured on TCP or SFS for 5 weeks, decellularized, and then prepared for viewing in the SEM and TEM as described in the Methods. Differences in cell morphology were observed in the SEM with the two culture environments (TCP, A & B; SFS, C & D). Evidence of SFS remodeling could be observed when scaffolds before (E) and after culture with the cells (C) were compared. TEM revealed a fibrillar ECM was deposited by the cells onto the SFS (F). White arrows (C, D, & F) indicate the location of ECM produced by the SM cells.

To determine whether pSGECs cultured on SFS produced a tissue-specific ECM, SM gland epithelial cells were treated with ascorbic acid during the last eight days of culture (i.e.: 8 days postconfluence). At harvest, the ECM was prepared for viewing by SEM and TEM after removal of the cells. When SM gland cells were cultured on TCP, they produced a thin layer of ECM (FIGS. 7 A & B). In contrast, when the same cells were cultured on SFS, they were able to produce an abundant 3-D ECM that covered the SFS (FIGS. 7 C & D). The fibrous nature of these proteins was clearly visible in the TEM (FIG. 7F). In addition, salivary cells remodel the SFS during culture. This can be seen by comparing the structure of the SFS after culture (FIG. 7C) with the original SFS not subjected to culture with the cells (FIG. 7E) (Kundu, et al., 2014; Marmary, et al., 1987).

By use of phase contrast and immunofluorescence microscopies, the presence of type IV collagen, a key basement membrane protein, was identified in cultures on SFS, but not TCP (FIG. 8). These results suggest that SFS promotes the formation of a 3-D ECM by SM gland epithelial cells, resulting in an environment that maintains many of the differentiated features of pSGECs.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aframian, et al., *Tissue Eng Part B Rev.* 14(2):187-98, 2008.
Athanasiou, et al., *Biomaterials.* 17(2):93-102, 1996.
Baum, *Adv Dent Res.* 14: 84-8, 2000.
Baum, *Ann NY Acad Sci.* 694: 17-23, 1993.
Busch, et al., *Arch Oral Biol.* 47(10):717-22, 2002.
Cancedda, et al., *Matrix Biol.* 22(1):81-91, 2003.
Chan, et al., *Biomaterials.* 33(2):464-72, 2012.
Chen, *Birth Defects Res C Embryo Today.* 90(1):45-54, 2010.
Chen, et al., *J Bone Miner Res.* 22(12):1943-56, 2007.
Chen, et al., *Tissue Eng.* 11(3-4):526-34, 2005.
Coppes & Stokman, *Oral Dis.* 17(2):143-53, 2011.

Costa, et al., *Int J Biochem Cell Biol.* 44(12):2233-7, 2012.
Crapo, et al., *Biomaterials.* 32(12):3233-43, 2011.
D'Avola, et al., *Ann Anat.* 188(5):431-8, 2006.
de Moraes, et al., *J Biomed Mater Res B Appl Biomater.* 102: 869, 2014.
Fujita-Yoshigaki, et al., *Cell Tissue Res.* 320: 455, 2005.
Harunaga, et al., *J Dent Res.* 90(9):1070-7, 2011.
Kadoya & Yamashina, *Anat Sci Int.* 80(2):71-9, 2005.
Kagami, et al., *Oral Dis.* 14(1):15-24, 2008.
Kundu, et al., *Progress in Polymer Science.* 39: 251, 2014.
Lai, et al., *Stem Cells Dev.* 19(7):1095-107, 2010.
Leal-Egana & Scheibel, *Biotechnol Appl Biochem.* 55(3): 155-67, 2010.
Lombaert, et al., *Oral Dis.* 17(5):445-9, 2011.
Maria, et al., *Tissue Eng Part A.* 17(9-10):1229-38, 2011.
Marmary, et al., *Comp Biochem Physiol A Comp Physiol.* 88: 307, 1987.
Mauney, et al., *Biomaterials.* 28: 5280, 2007.
Nagaoka, et al., *Ann Biomed Eng.* 38(3):683-93, 2010.
Napenas, et al., *Odontology.* 97(2):76-83, 2009.
Sarosiek, et al., *Am J Med Sci.* 308: 23, 1994.
Siritientong, et al., *AAPS PharmSciTech.* 12: 771, 2011.
Sofia, et al., *J Biomed Mater Res.* 54(1):139-48, 2001.
Widhe, et al., *Biomaterials.* 31: 9575, 2010.
Yeh, et al., *In Vitro Cell Dev Biol.* 27A(9):707-12, 1991.
Zhang, et al., *J Biol Chem.* 283(12):7580-9, 2008.

What is claimed is:

1. A method of forming a salivary tissue-specific extracellular matrix comprising:
culturing salivary gland cells on a silk fibroin scaffold; and
exposing the salivary gland cells to ascorbic acid.

2. The method of claim 1, wherein exposing the salivary gland cells to ascorbic acid is performed after the salivary gland cells achieve confluence.

3. The method of claim 2, wherein the salivary gland cells are exposed to ascorbic acid for eight days.

4. The method of claim 1, further comprising decellularizing the extracellular matrix.

5. The method of claim 1, wherein each dimension of the three-dimensional extracellular matrix measures at least 150 µm.

6. A method of producing differentiated salivary gland cells, the method comprising:
(a) generating a three-dimensional extracellular matrix by culturing salivary gland cells on a silk fibroin scaffold;
(b) decellularizing the extracellular matrix;
(c) incubating precursors of salivary gland cells with the decellularized three-dimensional extracellular matrix to produce differentiated salivary gland cells.

7. The method of claim 6, wherein the precursors of salivary gland cells are pluripotent stem cells.

8. The method of claim 7, wherein the pluripotent stem cells are mesenchymal stem cells.

9. The method of claim 6, wherein the extracellular matrix is essentially free of salivary gland cells before step (c).

10. The method of claim 6, wherein culturing the salivary gland cells in step (a) comprises growing the salivary gland cells to confluency.

11. The method of claim 6, wherein step (a) comprises exposing the salivary gland cells to ascorbic acid.

* * * * *